US010695036B2

(12) United States Patent
Allen et al.

(10) Patent No.: US 10,695,036 B2
(45) Date of Patent: Jun. 30, 2020

(54) MAGNETIC APPARATUS AND METHODS OF USE

(71) Applicant: University of Florida Research Foundation, Inc., Gainesville, FL (US)

(72) Inventors: Kyle Douglas Allen, Gainesville, FL (US); Jon Paul Dobson, Gainesville, FL (US); Elena Georgina Yarmola, Gainesville, FL (US); Zachary Kaufman, Plantation, FL (US); David P. Arnold, Gainesville, FL (US)

(73) Assignee: UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 342 days.

(21) Appl. No.: 15/236,552

(22) Filed: Aug. 15, 2016

(65) Prior Publication Data

US 2016/0345941 A1   Dec. 1, 2016

Related U.S. Application Data

(62) Division of application No. 13/967,571, filed on Aug. 15, 2013, now abandoned.
(Continued)

(51) Int. Cl.
*A61B 10/02* (2006.01)
*A61B 10/00* (2006.01)
(Continued)

(52) U.S. Cl.
CPC ............ *A61B 10/02* (2013.01); *A61B 10/00* (2013.01); *A61B 10/0045* (2013.01);
(Continued)

(58) Field of Classification Search
None
See application file for complete search history.

(56) References Cited

U.S. PATENT DOCUMENTS 7,632,638 B2   12/2009   Sauer-Budge et al.
8,118,754 B1 *   2/2012   Flynn ................. A61B 10/0233
                                                                128/897
(Continued)

OTHER PUBLICATIONS

Jason E Jaetao, et al.; Enhanced leukemia cell detection using a novel magnetic needle and nanoparticles; NIH Public Access; Cancer Res. Nov. 1, 2009; 69(21): 8310-8316. doi: 10.1158/0008-5472.CAN-09-1083; 16 pages.

*Primary Examiner* — Melanie Brown
*Assistant Examiner* — Richard Moerschell
(74) *Attorney, Agent, or Firm* — Thomas | Horstemeyer, LLP

(57) ABSTRACT

Provided herein is a magnetic apparatus for collecting superparamagnetic particles from a subject. The superparamagnetic particles are previously injected into the subject and have ligands bound thereto that are specific for one or more non-cell biomarkers. In one embodiment, the superparamagnetic particles are injected into and retrieved from a cavity such as a joint cavity. These compositions and methods allow for the sequestration and removal of inflammatory mediators, as both a diagnostic of the local immune response and a therapeutic that can reduce inflammation in the local disease environment.

20 Claims, 11 Drawing Sheets

Related U.S. Application Data

(60) Provisional application No. 61/683,267, filed on Aug. 15, 2012.

(51) Int. Cl.
*G01N 33/543* (2006.01)
*A61B 17/34* (2006.01)
*A61B 17/52* (2006.01)
*G01N 33/68* (2006.01)

(52) U.S. Cl.
CPC .......... *A61B 17/3421* (2013.01); *A61B 17/52* (2013.01); *G01N 33/54326* (2013.01); *G01N 33/6887* (2013.01); *G01N 2333/78* (2013.01); *G01N 2800/102* (2013.01); *G01N 2800/105* (2013.01); *Y10T 29/49* (2015.01)

(56) References Cited

U.S. PATENT DOCUMENTS

| | | | |
|---|---|---|---|
| 2002/0064829 A1* | 5/2002 | Yu | A61K 49/0004 435/69.1 |
| 2007/0037142 A1* | 2/2007 | Sauer-Budge | B01L 3/502761 435/5 |
| 2007/0154969 A1* | 7/2007 | Heinegard | G01N 33/6887 435/7.92 |
| 2007/0172897 A1* | 7/2007 | Maksymowych | G01N 33/6887 435/7.9 |
| 2012/0285832 A1* | 11/2012 | Guzman | G01N 27/44743 204/603 |

* cited by examiner

▲ Particles recovered after magnetic collection
▪ Dilutions of known concentrations of particles ◆ Dilutions of known Ab concentrations
▲ Particles recovered after magnetic collection

MAGNETIC APPARATUS AND METHODS OF USE

CROSS-REFERENCE TO RELATED APPLICATION

This application is a divisional and claims priority to U.S. Non-Provisional Patent Application entitled: "MAGNETIC APPARATUS AND METHODS OF USE, having Ser. No. 13/967,571, filed on Aug. 15, 2013, which claims priority to and the benefit of U.S. provisional application entitled "MAGNETIC APPARATUS AND METHODS OF USE", having Ser. No. 61/863,267, filed Aug. 15, 2012, both of which are hereby incorporated by reference in their entirety.

STATEMENT REGARDING FEDERALLY SPONSORED RESEARCH OR DEVELOPMENT

This invention was made with government support under AR057426 awarded by The National Institutes of Health. The government has certain rights in the invention.

BACKGROUND OF THE INVENTION

In damaged tissues, inflammatory mediators (such as cytokines or proteolytic enzymes) are up-regulated. These mediators are part of the wound healing response, but if up-regulated chronically, these mediators can cause a chronic inflammation that contributes to joint destruction. Osteoarthritis (OA) is the most prevalent disease in developed countries, affecting 27 million people in the U.S. (Lawrence R C, et al. (2008) *Arthritis Rheum* 58:26-35: Helmick C G, et al. (2008) *Arthritis Rheum* 58:15-25) and resulting in annual U.S. health care expenditures of $186 billion (Kotlarzz, et al, (2009) *Arthritis Rheum* 60:3546-3553). There is a critical lack of disease modifying OA drugs (DMOAD), due in part to an inability to clinically detect early stage OA. Though promising biomarkers in urine and serum have been identified through the OA Biomarkers Global Initiative, biochemical changes detectable in the urine or serum are not specific to an affected joint, are dilute relative to levels within the affected joint, and may not be detectable at the earliest stages of OA.

In order to accurately diagnose and assess OA in the earliest stages it is necessary to sample biomarkers in the affected joint, such as the knee. Harvesting biomarkers from the synovial fluid of the knee joint has proven to be challenging. In particular, removal of synovial fluid is difficult because it is an incredibly viscous fluid that usually requires a large needle for its removal. Use of a large needle is difficult in intermediate joints and impossible in smaller joints such as the metacarpalphalanges and facet joints. Removal of synovial fluid from large joints such as the knee or hip, while easier, is still problematic due to a fairly high rate of "dry taps" or inability to remove fluid from those joints.

Accordingly, there is a need for a magnetic micro/nanoparticle-based assay that can harvest biomarkers for diagnosis, prognosis, or treatment of a disease. More specifically, there is a need for a method wherein magnetic micro- and nanoparticles functionalized with molecules that target OA biomarkers are injected into the synovial cavity and harvested using a smaller apparatus and needle.

SUMMARY OF THE INVENTION

Provided herein are compositions and methods that solve the problems or inadequacies of the prior art. More specifically, provided herein are magnetic micro/nanoparticle-based compositions and assays that do not require removal of a cavitational fluid such as synovial fluid. The disclosed methods also provide an advantage in that they allow for the removal of small particles with magnetic properties from areas that are hard to access.

In several methods described herein, magnetic nanoparticles are functionalized with ligands specific for an inflammatory mediator. These particles are injected into the site of inflammation (e.g., the fluid-filled synovial cavity, in the case of osteoarthritis or ACL-rupture), allowing the particle/antibody to bind to inflammatory mediators. A high-field, high-gradient magnetic needle is then introduced into the site, and particles to which the inflammatory mediators are bound are collected from the site. Particles removed from the site of inflammation can be analyzed for the severity of the inflammatory response, and inflammation can be decreased by physically removing key inflammatory mediators from the site of inflammation. These compositions and methods eliminate the need to remove synovial fluid to access the biomarkers.

The term "magnetic needle" is used interchangeably herein with the term magnetic apparatus. The compositions comprise permanent magnets or magnetic needle tips that are fabricated on a micrometer scale and are either non-expandable or expandable. The non-expandable magnets preferably have a pyramidal or conical shape, whereas the expandable magnets are preferably outwardly expandable to maximize micro- or nanoparticle collection in vivo. Accordingly, it is to be understood that the term "magnetic needle" includes expandable embodiments unless the context of its use dictates otherwise.

A specific application of the compositions and methods disclosed herein involves extracting previously injected micro- or nanoparticles from an arthritic knee joint. Polymer-coated superparamgnetic nanoparticles or polymer/superparmagnetic composite microparticles (multiple superparmagnetic particles embedded within a diamagnetic polymer matrix) can be created with soft-magnetic materials (primarily iron oxides) that can also attach to certain biomarkers for arthritis. These particles can be injected into the synovial fluid of the knee where they will bond with the biomarkers and then extracted later with the magnetic needle. This allows for the biomarkers to be collected and analyzed without having to actually extract the synovia fluid from the knee.

The magnetic apparatuses described herein can also be used for actuation of magnetic micro- or nanoparticles for studies of mechanoactivation of cell surface receptors or targeting of magnetic micro- or nanoparticles carrying biomolecules to specific, individual cells within a cell culture or tissue slice.

BRIEF DESCRIPTION OF THE DRAWINGS

FIGS. 2(A and B) shows light microscopy images of two generations of laser-machined NdFeB pyramidal magnetic apparatuses on the end of a steel rod.

DETAILED DESCRIPTION OF THE INVENTION

Figure 1:
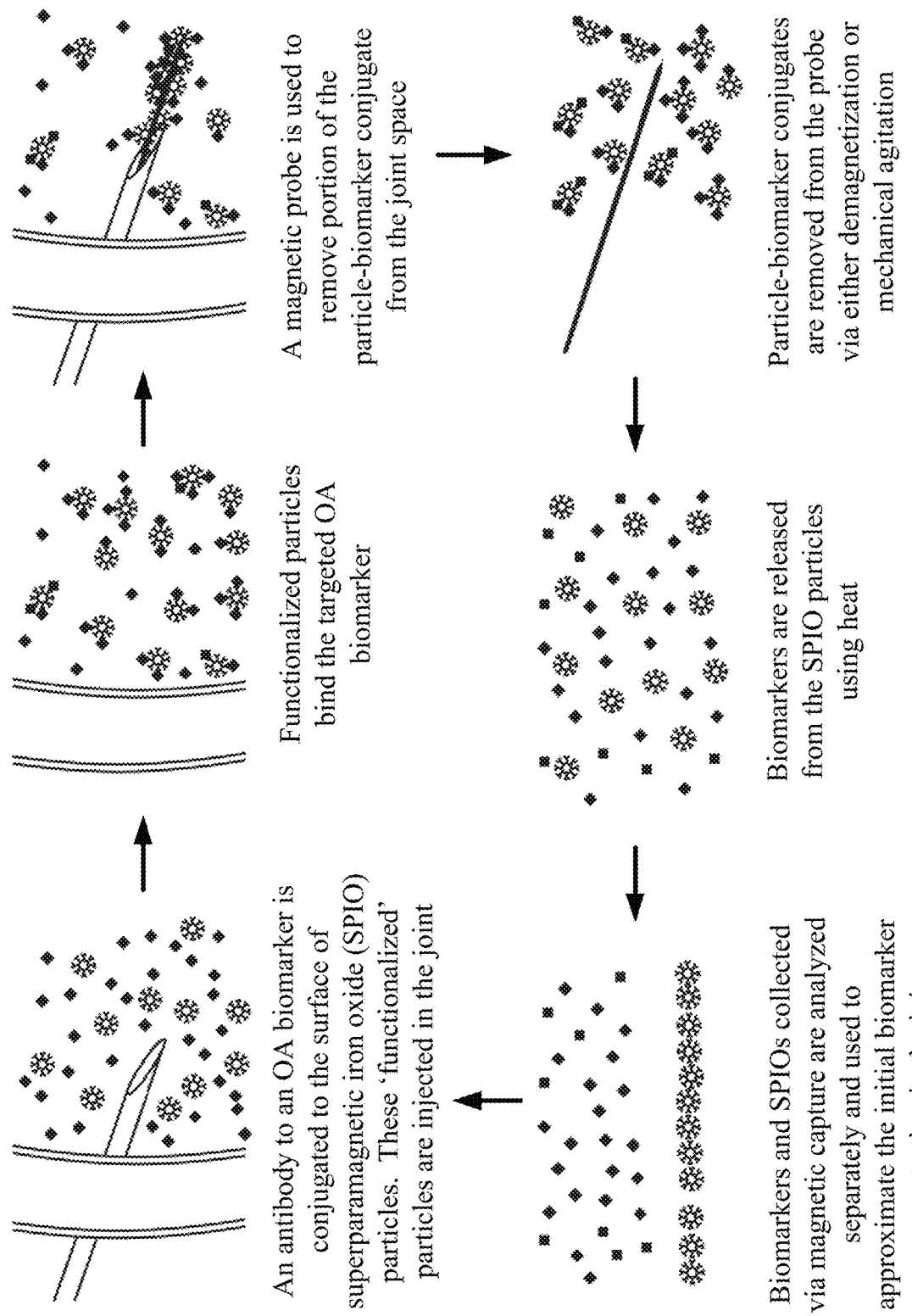
FIG. 1 is a schematic showing one embodiment of the magnetic capture technology.

Provided herein is a magnetic apparatus for collecting superparamagnetic micro- or nanoparticles from a subject. Such a magnetic apparatus is also referred to herein as a "microneedle," "magnetic needle," or "magnetic needle tip." The superparamagnetic particles are previously injected into the subject and have ligands bound thereto that are specific for one or more non-cell biomarkers. In a preferred embodiment, the superparamagnetic micro- or nanoparticles are injected into and retrieved from a cavity such as a joint cavity. These compositions and methods allow for the sequestration and removal of inflammatory mediators and disease biomarkers, as both a diagnostic of the local immune response and a therapeutic that can reduce inflammation in the local disease environment. FIG. 1 is a schematic showing one embodiment of these compositions and methods. Term definitions used in the specification and claims are as follows.

Definitions

As used in the specification and claims, the singular forms "a," "an" and "the" include plural references unless the context clearly dictates otherwise. For example, the term "a cell" includes a plurality of cells, including mixtures thereof.

When referring to a subject or patient, the term "administering" refers to an administration that is oral, topical, intravenous, subcutaneous, transcutaneous, transdermal, intramuscular, intra-joint, parenteral, intra-arteriole, intradermal, intraventricular, intracranial, intraperitoneal, intralesional, intranasal, rectal, vaginal, by inhalation or via an implanted reservoir. The term "parenteral" includes subcutaneous, intravenous, intramuscular, intra-articular, intraperitoneal, intra-synovial, intrasternal, intrathecal, intrahepatic, intralesional, and intracranial injections or infusion techniques. In some embodiments, the administration is intracaviteal.

The term "antibody" is used in the broadest sense and specifically covers monoclonal antibodies (including full-length monoclonal antibodies), polyclonal antibodies, and multispecific antibodies (e.g., bispecific antibodies). Antibodies (Abs) and immunoglobulins (Igs) are glycoproteins having the same structural characteristics. While antibodies exhibit binding specificity to a specific target, immunoglobulins include both antibodies and other antibody-like molecules which lack target specificity. Native antibodies and immunoglobulins are usually heterotetrameric glycoproteins of about 150,000 Daltons, composed of two identical light (L) chains and two identical heavy (H) chains. Each heavy chain has at one end a variable domain ($V_H$) followed by a number of constant domains. Each light chain has a variable domain at one end ($V_L$) and a constant domain at its other end. An antibody "specific for" another substance binds, is bound by, or forms a complex with that substance.

The term "antibody fragment" refers to a portion of a full-length antibody, generally the target binding or variable region. Examples of antibody fragments include Fab, Fab', F(ab')$_2$ and Fv fragments. The phrase "functional fragment or analog" of an antibody is a compound having qualitative biological activity in common with a full-length antibody. For example, a functional fragment or analog of an anti-IgE antibody is one which can bind to an IgE immunoglobulin in such a manner so as to prevent or substantially reduce the ability of such a molecule from having the ability to bind to the high affinity receptor, FcERI. As used herein, "functional fragment" with respect to antibodies refers to Fv, F(ab) and F(ab')$_2$ fragments. The Fab fragment contains the constant domain of the light chain and the first constant domain (CH1) of the heavy chain. Fab fragments differ from Fab fragments by the addition of a few residues at the carboxyl terminus of the heavy chain CH1 domain including one or more cysteines from the antibody hinge region. F(ab') fragments are produced by cleavage of the disulfide bond at the hinge cysteines of the F(ab')$_2$ pepsin digestion product. Additional chemical couplings of antibody fragments are known to those of ordinary skill in the art. An "Fv" fragment is the minimum antibody fragment which contains a complete target recognition and binding site. This region consists of a dimer of one heavy and one light chain variable domain in a tight, non-covalent association ($V_H$-$V_L$ dimer). It is in this configuration that the three CDRs of each variable domain interact to define a target binding site on the surface of the $V_H$-$V_L$ dimer. Collectively, the six CDRs confer target binding specificity to the antibody. However, even a single variable domain (or half of an Fv comprising only three CDRs specific for a target) has the ability to recognize and bind to a target, although at a lower affinity than the entire binding site. "Single-chain Fv" or "sFv" antibody fragments comprise the $V_H$ and $V_L$ domains of an antibody, wherein these domains are present in a single polypeptide chain. Generally, the Fv polypeptide further comprises a polypeptide linker between the $V_H$ and $V_L$ domains, which enables the sFv to form the desired structure for target binding.

As used herein, the term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

"Humanized" forms of non-human (e.g. murine) antibodies are chimeric immunoglobulins, immunoglobulin chains or fragments thereof (such as Fv, Fab, Fab', F(ab')$_2$ or other target-binding subsequences of antibodies) that contain minimal sequence derived from non-human immunoglobulin. In general, the humanized antibody will comprise substantially all of at least one, and typically two, variable domains in which all or substantially all of the CDR regions correspond to those of a non-human immunoglobulin and all or substantially all of the FR regions are those of a human immunoglobulin consensus sequence. The humanized antibody may also comprise at least a portion of an immunoglobulin constant region (Fc), typically that of a human immunoglobulin template chosen.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single target site. Furthermore, in contrast to conventional (polyclonal) antibody preparations which typically include different antibodies directed against different determinants (epitopes), each monoclonal antibody is directed against a single determinant on the target. In addition to their specificity, monoclonal antibodies are advantageous in that they may be synthesized by the hybridoma culture, uncontaminated by other immunoglobulins. The modifier "monoclonal" indicates the character of the antibody as being obtained from a substantially homogeneous population of antibodies, and it is not to be construed as requiring production of the antibody by any particular method.

The terms "polynucleotide" and "oligonucleotide" are used interchangeably and refer to a polymeric form of nucleotides of any length, either deoxyribonucleotides or ribonucleotides, or analogs thereof. Polynucleotides may have any three-dimensional structure and may perform any function, known or unknown. The following are non-limiting examples of polynucleotides: a gene or gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, polynucleotide probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. The term also refers to both double- and single-stranded molecules. Unless otherwise specified or required, any embodiment of this invention that is a polynucleotide encompasses both the double-stranded form and each of two complementary single-stranded forms known or predicted to make up the double-stranded form.

The term "polypeptide" is used in its broadest sense to refer to a compound of two or more subunit amino acids, amino acid analogs, or peptidomimetics. The subunits may be linked by peptide bonds. In another embodiment, the subunit may be linked by other bonds, e.g., ester, ether, etc. As used herein the term "amino acid" refers to either natural and/or unnatural or synthetic amino acids, including glycine and both the D or L optical isomers, and amino acid analogs and peptidomimetics. A peptide of three or more amino acids is commonly called an oligopeptide if the peptide chain is short. If the peptide chain is long, the peptide is commonly called a polypeptide or a protein.

"Selectively binds" refers to a non-specific binding event as determined by an appropriate comparative control. Binding is selective when the binding is at least 10, 30, or 40 times greater than that of background binding in the comparative control.

A "subject," "individual," or "patient," used interchangeably herein, refers to a vertebrate, preferably a mammal, more preferably a human. Mammals include, but are not limited to, murines, simians, humans, farm animals, sport animals, and pets.

The term "superparamagnetic particle" includes both micro- and nanoparticle sized materials. In some embodiments, a superparamagnetic particle is spherical and ranges in diameter between 100 nm and 2000 nm. The term "superparamagnetic" refers in some embodiments to a spherical material containing iron oxide and having a diameter of less than approximately 30 nm. Accordingly, a superparamagnetic particle includes, but is not limited to, a superparamagnetic iron oxide nanoparticle (SPION). A superparamagnetic particle can be embedded in any suitable polymer including, but not limited to, polystyrene, polylactic acid, and polyglycolic acid.

Description

Figure 2A:
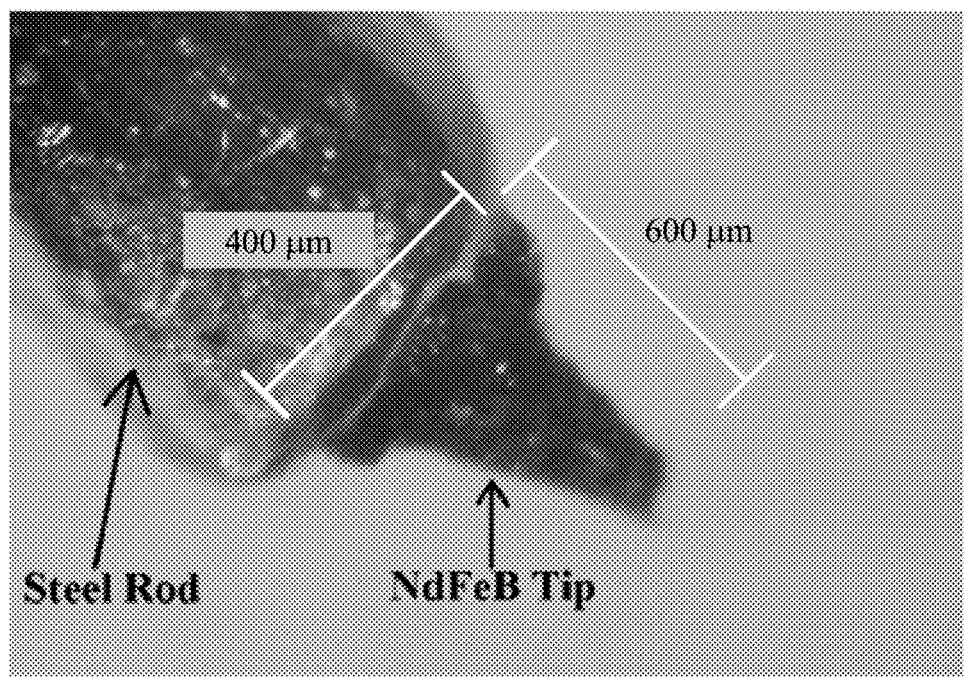
FIG. 2A shows a first-generation magnetic apparatus and FIG. 2B shows a second-generation magnetic apparatus.
Figure 2B:
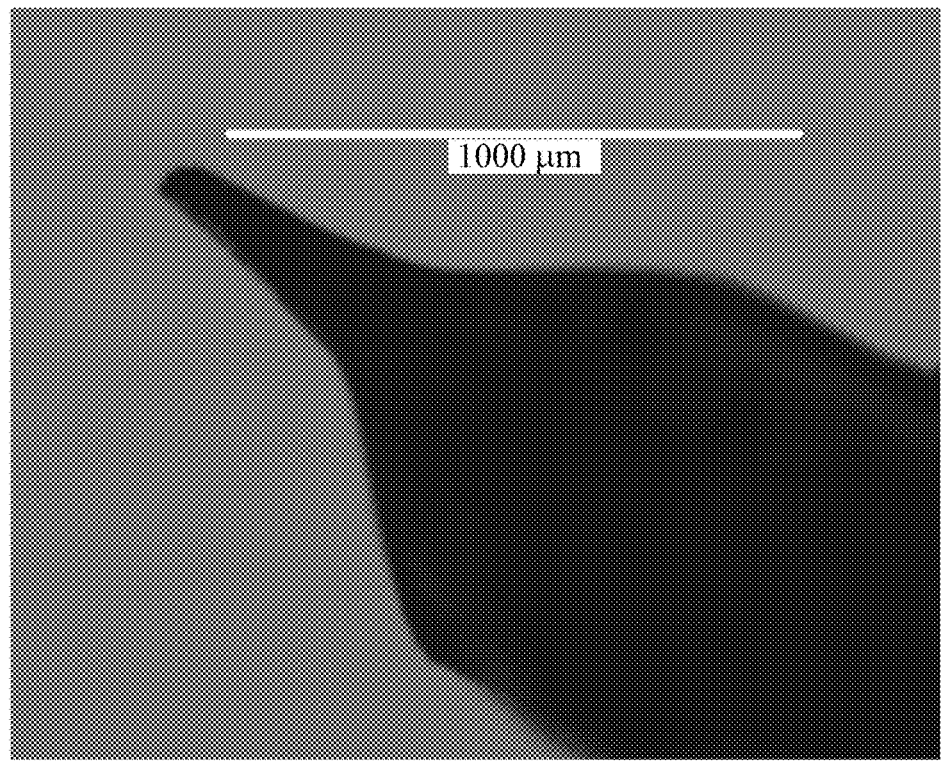

One magnetic apparatus described herein comprises a permanent magnet between 500 and 1000 microns in height and having proximal and distal ends. The permanent magnet can be non-expandable or expandable. As used herein, the term "non-expandable" refers to a magnet that does not itself expand outwardly. A non-expandable magnet can however be moved vertically within a cannulae for placement into a body cavity or tissue. A non-expandable permanent magnet is preferably widest at the proximal end and narrowest at the distal end. Accordingly, a permanent magnet can be pyramidal or conical in shape. FIG. 2 shows examples of a pyramidal permanent magnet on the end of a soft-magnet rod. FIG. 2A shows a first generation pyramidal permanent magnet and FIG. 2B shows a second generation pyramidal permanent magnet, both placed at the end of a steel rod.

Figure 3A:
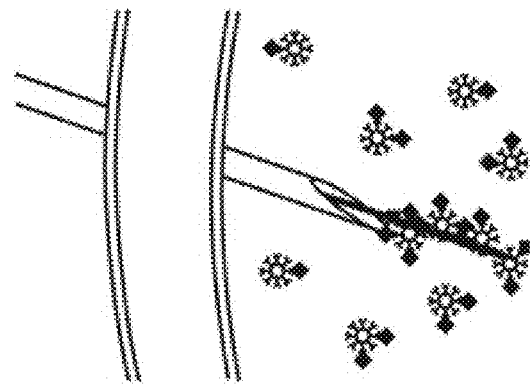
FIG. 3(A-C) is a schematic showing an example of a non-expandable (FIG. 3A), mop-like expandable (FIG. 3B), and balloon-catheter expandable (FIG. 3C) magnetic apparatus.
Figure 3B:
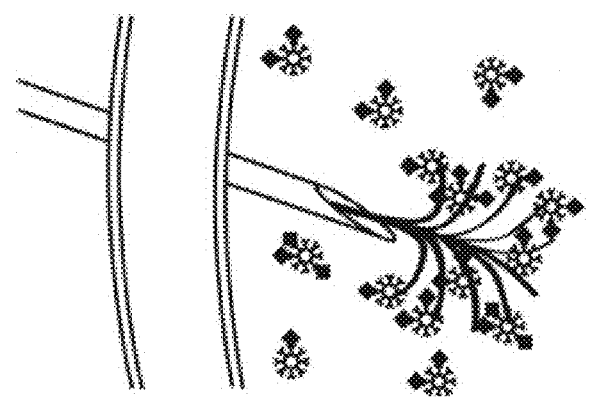
Figure 3C:
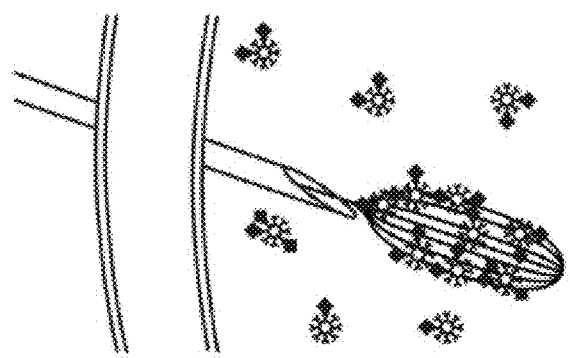

The expandable magnetic apparatuses described herein can have varying shapes, which maximize the collection of superparamagnetic micro- or nanoparticles. Two examples of outwardly expandable magnets are of a mop-type expansion and a balloon catheter-type expansion as shown in FIGS. 3B and 3C. In some embodiments, the expandable magnetic apparatus is threaded down a hollow cannulae and then expanded and contracted in the fluid space.

In one embodiment, a non-expandable magnetic apparatus has a distal end tip that is between 30 and 80 microns in width, and preferably approximately 50 microns in width. The proximal end of the magnetic apparatus can be anywhere between 200 and 500 microns in width, and preferably approximately 400 microns in width. The narrow nature of the distal end tip is important as this allows for collection of superparamagnetic nanoparticles that are attached to non-cell biomarkers such as inflammatory mediators and collagen degradation products discussed in more detail below.

The magnetic apparatus described herein can be made of any permanent magnet material. In one embodiment, the permanent magnet material comprises neodymium, iron and boron, and more preferably comprises an alloy having the chemical formula of $Nd_2Fe_{14}B$. In some embodiments, the permanent magnet apparatus is made by a method comprising rotating a laser beam at a surface of a permanent magnet sheet in 90 degree steps to achieve a pyramidal shaped permanent magnet between 500 and 1000 microns in height. Example 1 describes one such embodiment. In this example, a magnetic apparatus is created that has proximal and distal ends, wherein a tip of the distal end is between 30 and 80 microns in width and the proximal end is between 200 and 500 microns in width.

In some embodiments, the magnetic apparatus is placed at the distal end of a rod having soft magnetic properties. FIG. 2 shows several examples of such assembly. In further embodiments, the magnetic apparatus and steel rod are placed within a cannulae for penetrating a cavity or tissue of a subject. The cannulae has openings at a distal and proximal end with the cross-sectional area in between the distal end and the proximal end being substantially hollow and containing the magnetic apparatus and the rod, wherein the magnetic apparatus is positionable outside of the distal end of the cannulae and within the cavity or tissue of the subject. This magnetic apparatus assembly can be used to collect from the subject superparamagnetic micro- or nanoparticles that have been previously injected into the subject.

The compositions and methods described herein are particularly advantageous for collection and/or retrieval of non-cell biomarkers from in vivo tissues or cavities. These methods can be used for the assessment of local tissue changes including early diagnosis of an inflammatory disease such as arthritis. Since osteoarthritis is a disease mediated by local catabolic and inflammatory responses, measurement of inflammatory biomarkers from directly within the joint space allows for such early diagnosis. Accordingly, provided herein are methods for diagnosing, or determining the progression of, an inflammatory disease including, but not limited to, arthritis. The compositions and methods described herein can also be used for treatment of inflammatory and other diseases through the removal of non-cell biomarkers. It should be understood, however, that the technology described herein is not limited to a single disease state or a specific inflammatory mediator, as the superparamagnetic nanoparticles can be designed to target multiple mediators and can be delivered to multiple disease sites.

The local tissue change and/or disease presence or progression is measured via a determination of the level or amount of a non-cell biomarker collected from a tissue or cavitational fluid. One example of a cavitational fluid is a synovial fluid. Non-cell biomarkers include, but are not limited to, a polynucleotide, a polypeptide, or a fragment thereof. The term "non-cell" refers herein to biomarkers that are not bound to a cell upon collection or retrieval. Exemplary non-cell biomarkers for arthritis are urinary C-terminal telopeptides of type II collagen (uCTX-II); serum cartilage oligomeric matrix protein (COMP); serum hyaluronan (HA); serum and urine C1, 2C (another collagen fragment); serum and urine C2C (another collagen fragment); serum and urine Coll2-1 and Coll2-1NO2 (another collagen fragment); serum CPII (another collagen fragment); serum Procollagen type II N-terminal propeptide (PIIANP, another collagen fragment); urine/serum NTX-1 (another collagen fragment); urine/serum CTX-1 (another collagen fragment); serum CS846 (aggrecan fragment); and serum matrix metalloproteinase 3 (MMP-3, proteolytic enzyme).

In some embodiments, the non-cell biomarker polypeptide is an inflammatory mediator, a collagen degradation product, a proteolytic enzyme, or a fragment thereof. The inflammatory mediator can be, but is not limited to, an interleukin including interleukin-1 and interleukin-6, tumor necrosis factor, a prostaglandin including prostaglandin E, or interferon gamma. Exemplary collagen degradation products are C-terminal fragments of Type II collagen and fragments of cartilage oligomeric matrix protein (COMP). Exemplary proteolytic enzymes are matrix metalloproteinase-1 (MMP1), MMP2, MMP3, MMP9, MMP13, a disintegrin and metalloproteinase with thrombospondin motifs-4 (ADAMTS4), and ADAMTS5. Accordingly, in some embodiments, the compositions and methods described herein are used to collect inflammatory mediators and/or collagen degradation products from the synovial fluid within a joint. Either no synovial fluid or a negligible amount of synovial fluid is removed from the joint, thus providing a significant advantage over prior art methods. In some embodiments, less than 100 µl, 50 µl, 25 µl, 10 µl, or 5 µl of synovial fluid is removed from the joint upon collection of one or more non-cell biomarkers from a joint of a subject using the magnetic apparatus of the present invention.

Some methods of collecting superparamagnetic nanoparticles bound to one or more non-cell biomarkers from a subject comprise inserting a magnetic apparatus into a cavity of the subject, wherein the magnetic apparatus comprises a permanent magnet between 500 and 1000 microns in height and having proximal and distal ends and wherein the magnetic apparatus is located at the distal end of a soft magnetic rod (or other rod-like implement). In this method, the magnetic apparatus and rod are moved through a cannulae for penetrating a cavity of the subject, the cannulae having openings at a distal and proximal end with the cross-sectional area in between the distal end and the proximal end being substantially hollow and containing the magnetic apparatus and the rod, wherein the magnetic apparatus is positionable outside of the distal end of the cannulae and within the cavity of the subject.

In these methods, the subject has been previously administered the superparamagnetic particles having a ligand specific for the one or more non-cell biomarkers. As used herein, the term "ligand" refers to any moiety that specifically binds to a non-cell biomarker. The term "ligand" includes, but is not limited to, an antibody and an aptamer (including polypeptide, DNA and RNA aptamers). Administration can be via any route, and in some embodiments, is via injection into the cavity to be tested.

The methods described herein can include the use of any magnetic apparatus described above or below, including both expandable and non-expandable embodiments of a magnetic apparatus. In preferred embodiments of the methods, the magnetic apparatus is a permanent NdFeB magnet that is widest at the proximal end and narrowest at the distal end and has a conical or pyramidal shape. More preferably, the tip of the distal end is between 30 and 80 microns in width, and preferably approximately 50 microns in width, and the proximal end is between 200 and 500 microns in width, and preferably approximately 400 microns in width.

It should be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims. Furthermore, all patents, published patent applications, and journal article publications recited herein are hereby incorporated by reference in their entirety for all purposes.

EXAMPLES

Example 1

Manufacture of Magnetic Needle Tip

A magnetic needle tip was laser-machined from an NdFeB permanent magnet using a diode-pumped solid-state laser operating at a normal 10-15 picosecond pulse width and 355 nm wavelength. An 800-micron-thick disc of NdFeB was placed under the laser, and the laser cut down through the thickness of the disc starting with a 50×50 micron square at the top and reaching a base of approximately 500×500 microns. This resulted in a pyramidal shape with a height of approximately 800 microns and a tip width of approximately 50 microns.

Figure 4:
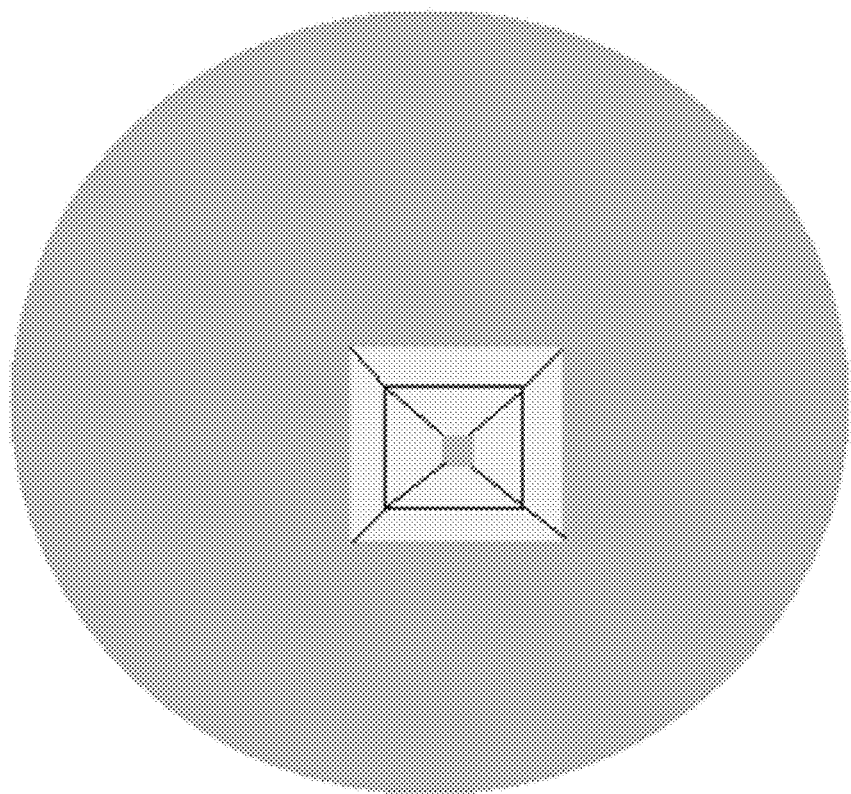
FIG. 4 is a schematic showing the laser cutting process.

During the above process, the laser remains nearly perpendicular to the magnet. The pyramidal shape is achieved by using the aspect ratio (shadowing effect). The laser starts at the top of the magnet with a very small square (shown in dark grey in the middle of the "X" in FIG. 4), and as the laser cuts deeper into the magnet, the square expands due to aspect ratio limitations. By the time the laser cuts all the way through the magnet, a larger square at the bottom is created which results in a nearly-pyramidal shape. The light gray area in the picture shows the path that the laser is actually cutting. It starts as a wide path and narrows to the size of the black square when it reaches the bottom.

Once the needle tip was machined, it was assembled onto a rod with soft-magnet properties such as a paperclip. See FIG. 2. First, the tip of the rod was dipped into an adhesive and then brought close to the base of the needle tip. The tip naturally attracted to the rod due to the magnetic force, and the adhesive then dried to keep the tip in place more permanently. This procedure of self-assembly could be reproduced at a large scale in manufacturing.

Example 2

Determination of Efficiency of Magnetic Particle Harvesting

Figure 5:
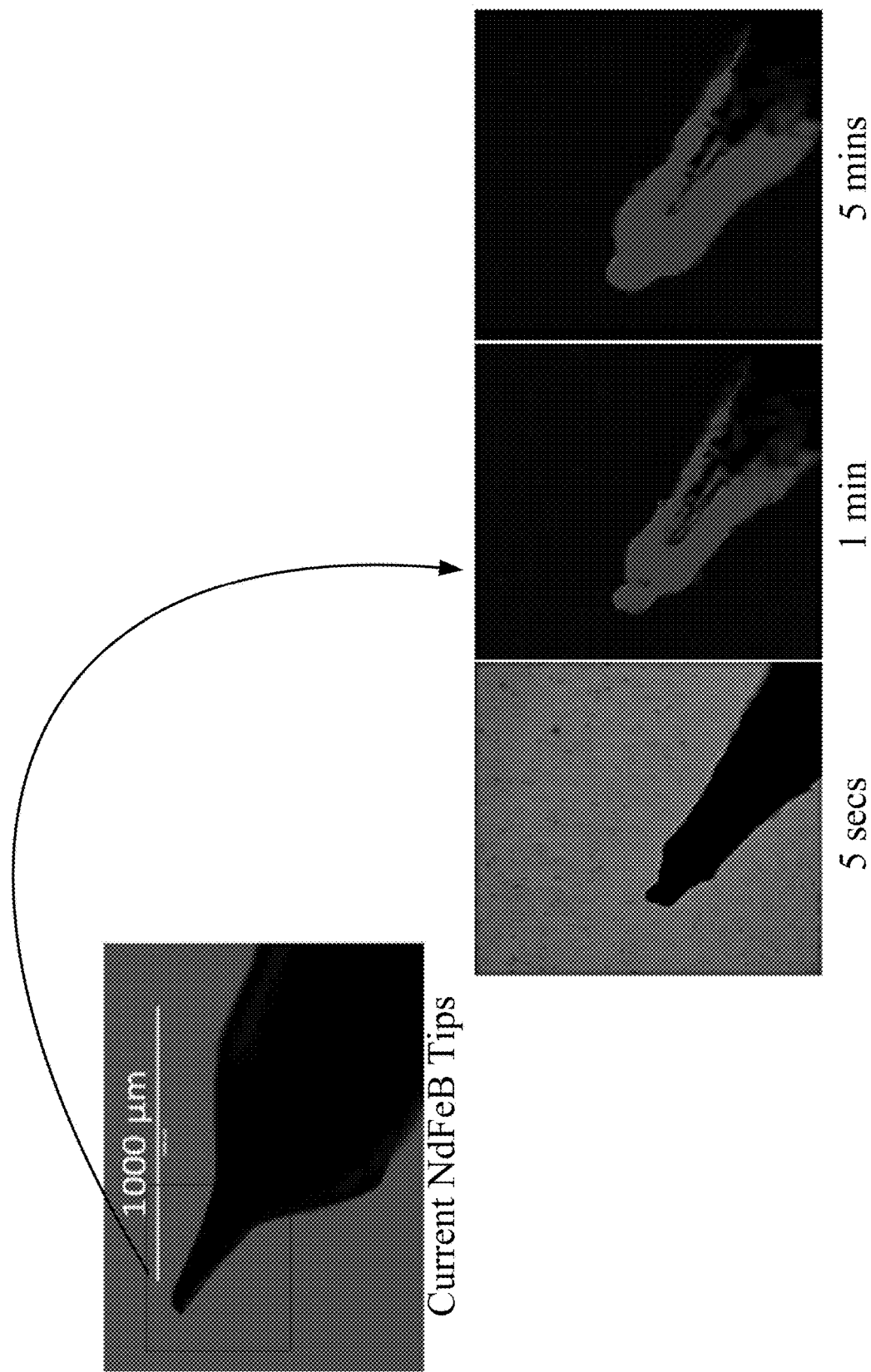
FIG. 5 is a fluorescent microscope image showing magnetic microspheres harvested by a magnetic apparatus described herein.

Microneedles were placed in a solution of polystyrene/iron oxide composite fluorescent superparamagnetic particles with approximately 30,000 particles/μL (1 μm particle diameter). Particles collecting on a magnetic needle can be seen in frame grabs from a video. In this experiment, microneedles were able to collect 100,000-900,000 microparticles from the solution. FIG. 5 shows the results of this assay, which demonstrate that NdFeB magnetic microneedles can collect polymeric particles with SPIONs embedded within the particle core.

Example 3

Time Dependencies for Binding and Release of the CTX-II Biomarker to/from Anti-CTX-II Conjugated Magnetic Particles Approximately 106 million of anti-CTX-II conjugated magnetic particles (approximately 220 antibody molecules per particle) were mixed with ether non-treated or hyaluronidase-treated bovine synovial fluid (SF) and subject to constant gentle mixing (final volume 900 μl). FIG. 6 shows that after 2.5 hours (6B) or indicated time intervals (6A), 100 μl aliquots were taken for analysis.

Figure 9:
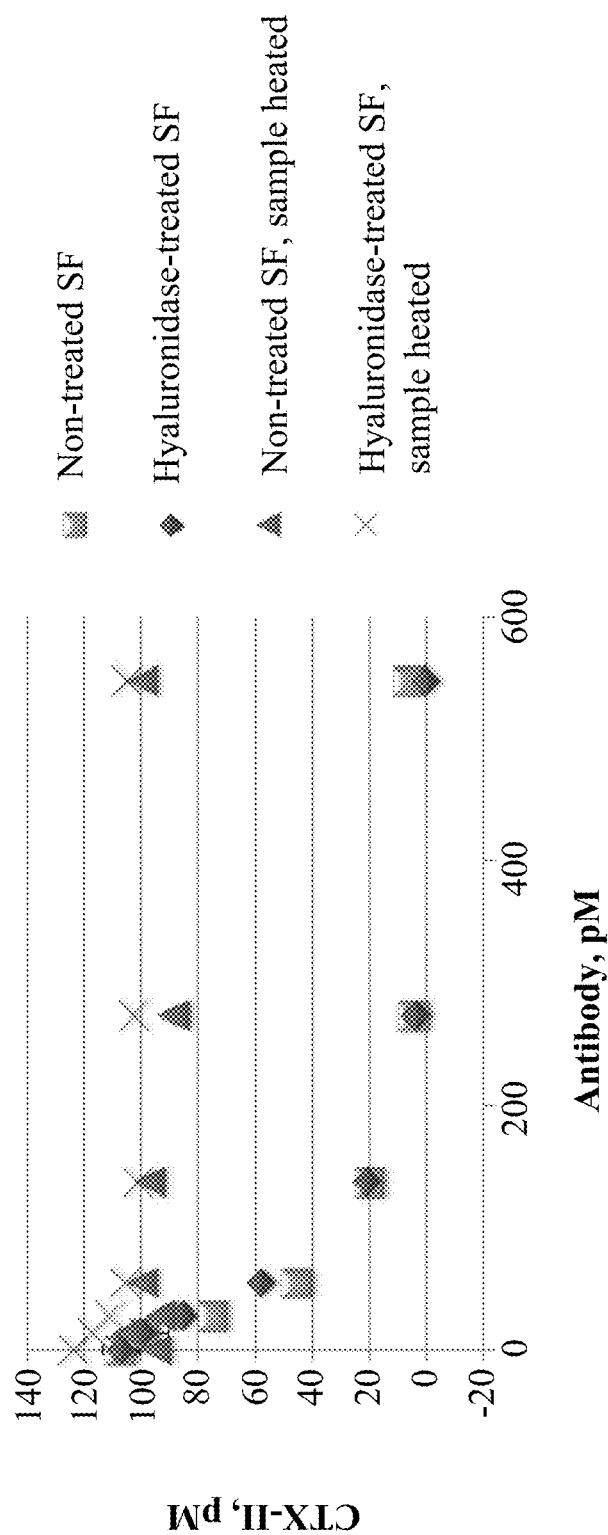
FIG. 9 is a graph showing the release of biomarker from antibody with heat.

Particles were separated from synovial fluid by centrifugation. Pellets were washed with PBS containing 0.05% TWEEN-20, 2% BSA, and 2 mM EDTA for 1 minute (6A) or for indicated amounts of time (6B). Then bound CTX-II was released from the particles by heating for 3 minutes at 85° C. (see control experiment shown in FIG. 9). Samples were analyzed for CTX-II using Serum Pre-Clinical CartiLaps ELISA kit. These results show no dependence on the synovial fluid viscosity.

Example 4

Collection of the CTX-II Biomarker with Magnetic Needle

Figure 7:
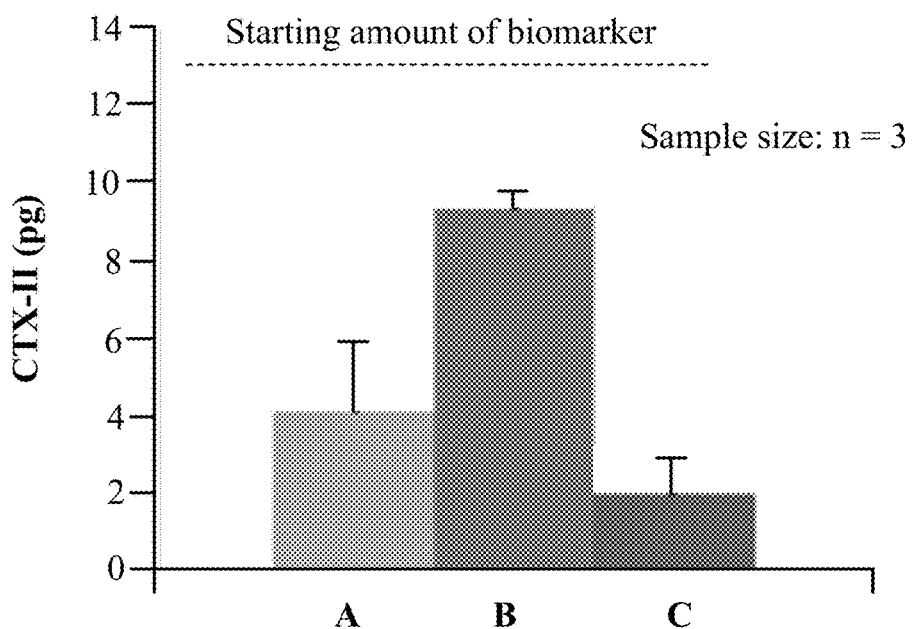
FIG. 7 is a bar graph showing collection of the CTX-II biomarker with a magnetic apparatus.
Figure 11A:
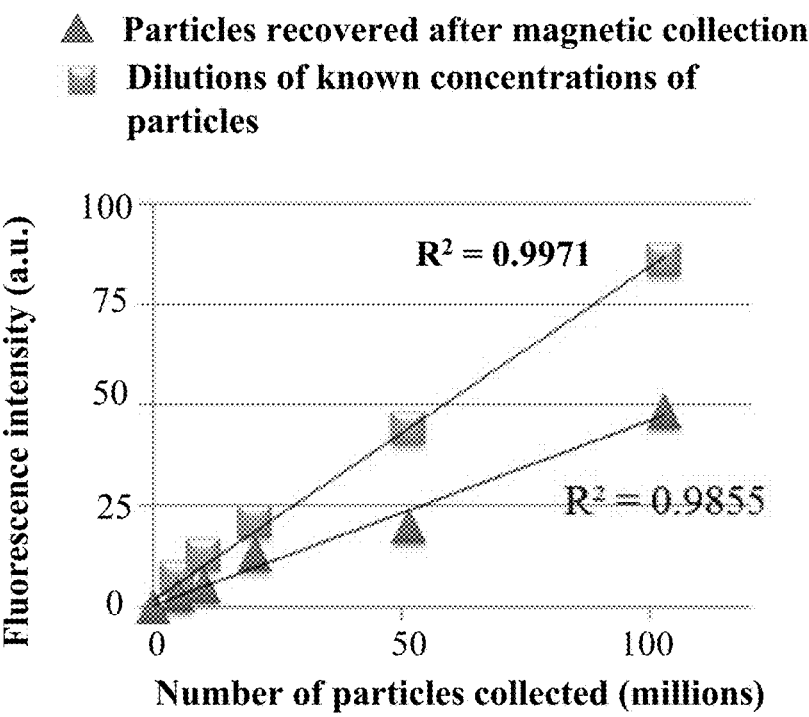
FIGS. 11(A and B) provides graphs demonstrating the amount of particles and attached antibody collected from the magnetic apparatus.

Approximately $10^8$ of the anti-CTX-II conjugated particles (approximately 170 antibody molecules per particle) were mixed with 130 μL of hyaluronidase-treated bovine synovial fluid containing 13.2 pg CTX-II biomarker and allowed to bind the biomarker. Particles were collected from synovial fluid using a NdFeB microneedle for 5 minutes. The remaining fluid and uncollected particles were separated using a magnetic plate. Collected particles were diluted in 35 μL PBS containing 0.05% TWEEN-20, 2% BSA, and 2 mM EDTA. 1 μL of sample were used for antibody quantification analysis (see FIG. 11), with the remaining 34 μL of sample heated at 85° C. for 3 minutes to release CTX-II (see FIG. 9). Samples were cooled to room temperature and centrifuged at 18,000 g for 10 minutes. Supernatants were analyzed for CTX-II using Serum Pre-Clinical CartiLaps ELISA kit. In FIG. 7, A: CTX-II remaining in supernatant; B: CTX-II bound to particles but not collected via the magnetic microneedle; C: CTX-II bound to particles and collected via the magnetic microneedle.

Example 5

Release of Particles from Magnetic Needle

Figure 8:
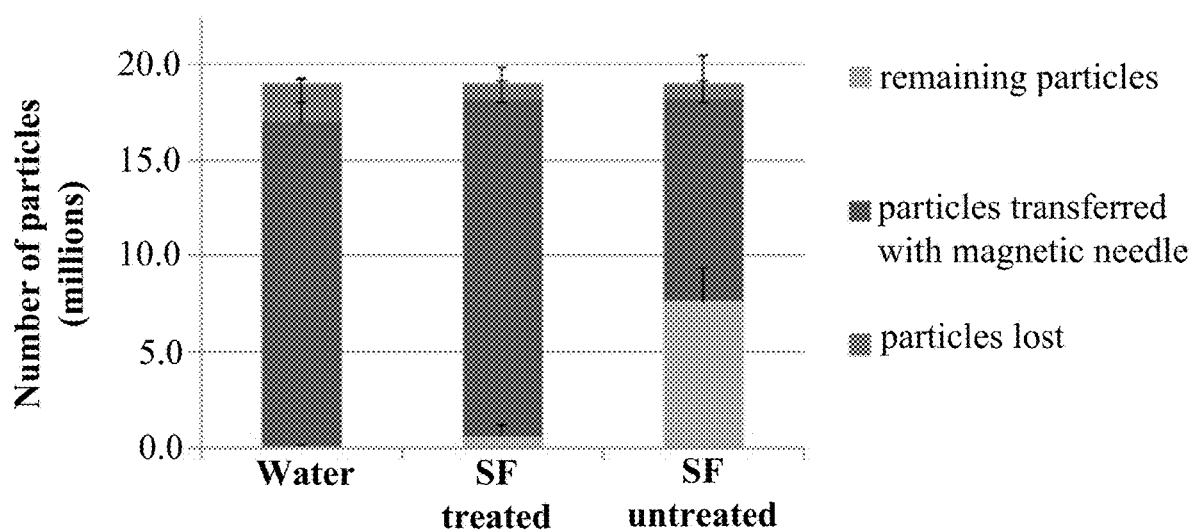
FIG. 8 is a bar graph showing release of particles from a magnetic apparatus.

Approximately 19 million of the 1.4 μm magnetic particles were diluted in 25 μl of water or bovine synovial fluid (SF) and mixed. SF was either treated with hyaluronidase to reduce viscosity (treated) or untreated. A magnetic needle was inserted into each sample, and particles were allowed to bind to the needle for 15 minutes. Then needles were removed and bound particles were washed out from the needles with 200 μL of turbulent water in the presence of strong magnetic field (magnetic plate). FIG. 8 shows the particles released from the needles and those that remained uncollected, which were quantified using the fluorescence intensity measurements. Control samples (without the needle transfer) were used to calculate the amounts of particles that were lost in the procedure: differences between control samples and total amount of collected particles are shown with gray color. Error bars on the plot show standard deviation for samples done in triplicate.

Example 6

Release of Biomarker from Antibody with Heat

Bovine synovial fluid (SF) was either treated with hyaluronidase to reduce viscosity or untreated. Amounts of free anti-CTX antibody indicated in FIG. 9 were added to each sample, mixed, and incubated for 2 hours. Indicated samples were heated at 85° C. for 3 minutes. Error bars on the plot show standard deviation for samples done in triplicate.

Example 7

Method of Determination of Biomarker Concentration Based on the Law of Mass Action Since dissociation of biomarker from the antibody-conjugated particles is very slow, the ratio of bound biomarker to total antibody after magnetic collection is equivalent to the ratio of bound biomarker to total antibody during collection. The law of mass action gives an expression for the equilibrium dissociation constant $K_d$, a characterization of binding strength of the reacting substances at dynamic equilibrium. In the equations shown below, B represents free (not bound to antibody) epitope on the biomarker, A represents free recognition site on the antibody, and AB represents a complex of the recognition site on the antibody and the biomarker epitope. [A], [B], and [AB] are concentrations of the corresponding substances.

$$[B]=K_d \cdot [AB]/[A]$$

$$[B]=K_d \cdot r/(1-r)$$

where $$r=[AB]/[A]_{total}$$

$$[A]_{total}=[AB]+[A]$$

$$0<r<1$$

Figure 6A:
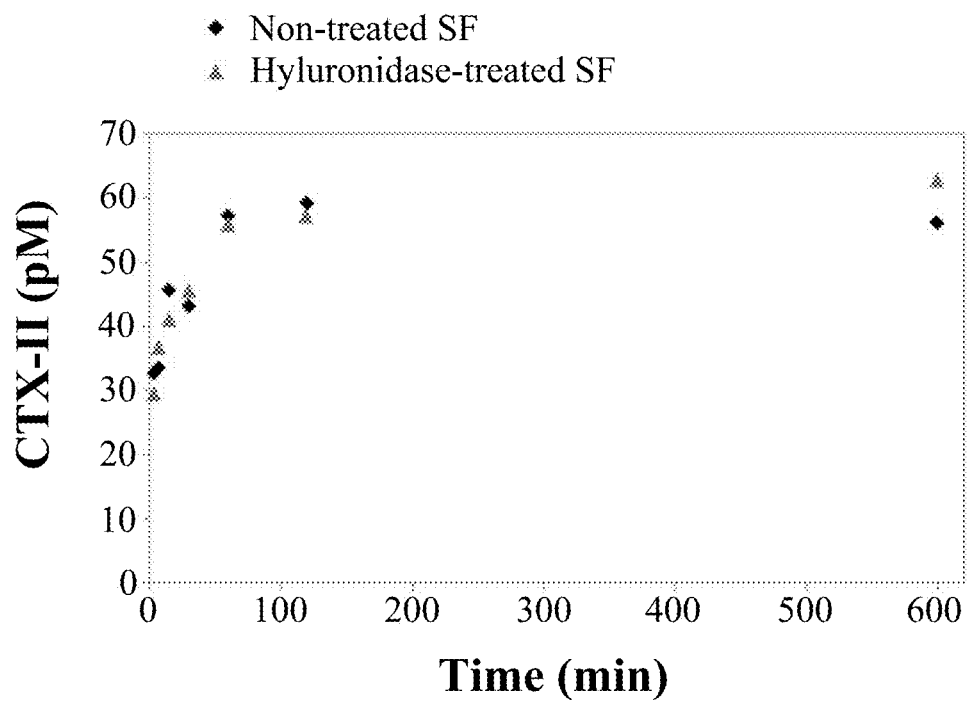
FIGS. 6(A and B) contains graphs showing time dependencies for binding and release of the CTX-II biomarker to/from anti-CTX-II conjugated magnetic particles.
Figure 6B:
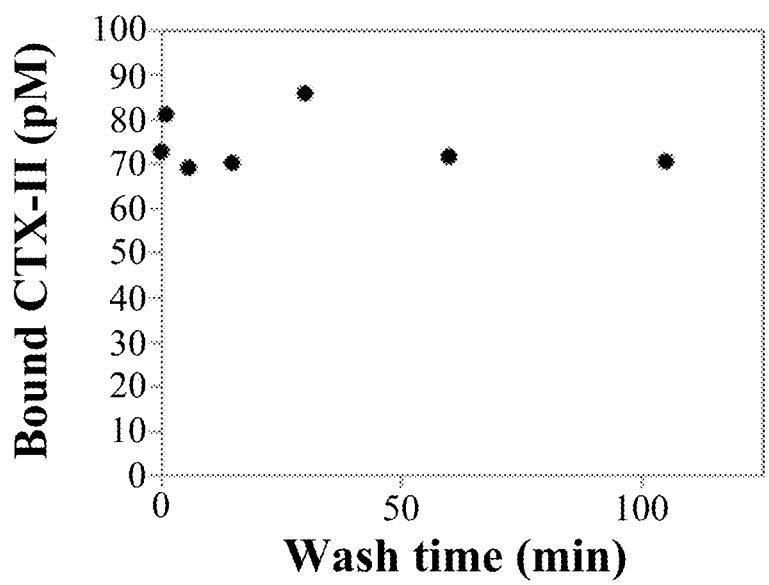
Figure 10:
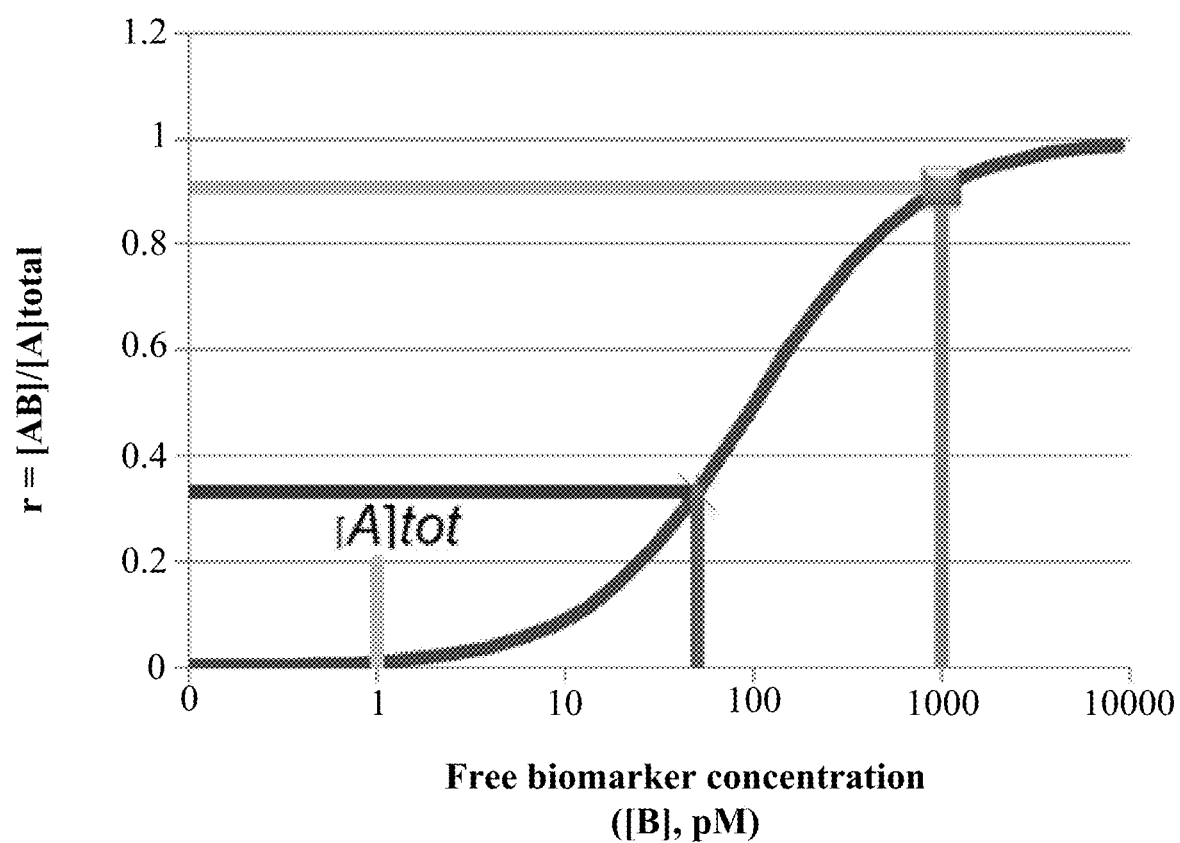
FIG. 10 shows a sample calibration curve for determining biomarker concentration.

The graph in FIG. 10 shows a theoretical binding (calibration) curve corresponding to $K_d$=100 pM. The initial biomarker concentration within the joint can be determined using this curve and ratio r, which is obtained from the analysis of the magnetically collected material, providing that a dynamic equilibrium between the antibody and biomarker is achieved prior to magnetic collection (FIGS. 6A & 6B).

Example 8

The Amount of Collected Particles and Attached Antibody

Figure 11B:
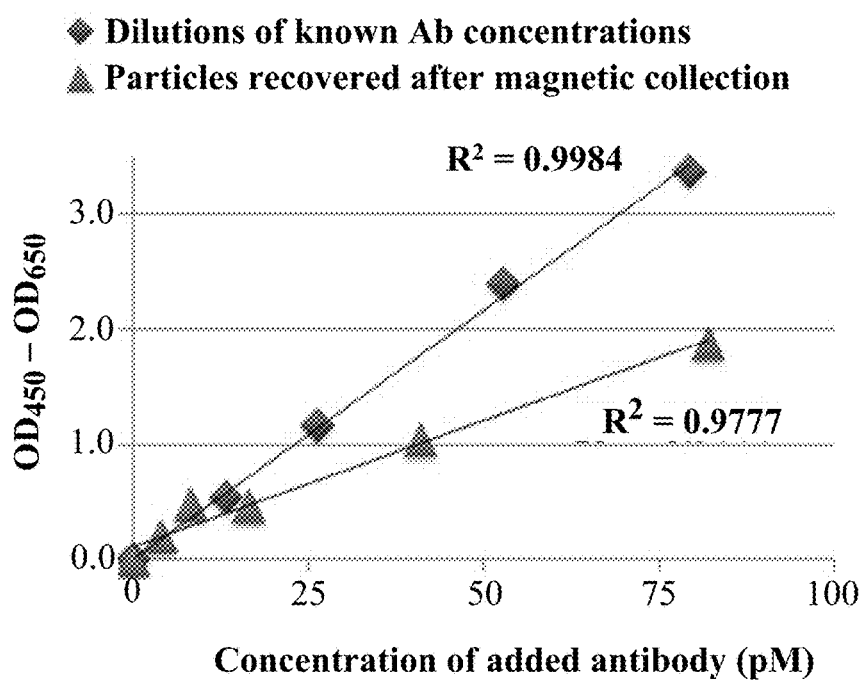

The amount of collected particles was quantified using fluorescence (FIG. 11A), or using a reaction of the TMB substrate (3,3',5,5'-tetramethylbenzidine) and the horseradish peroxidase (HRP) conjugated to the anti-CTX-II antibody (FIG. 11B). The readings were then compared to the solution of known antibody concentrations. The amount of collected biomarker was determined by ELISA.

Example 9

Calibration Curve for $K_d$ Determination

Figure 12:
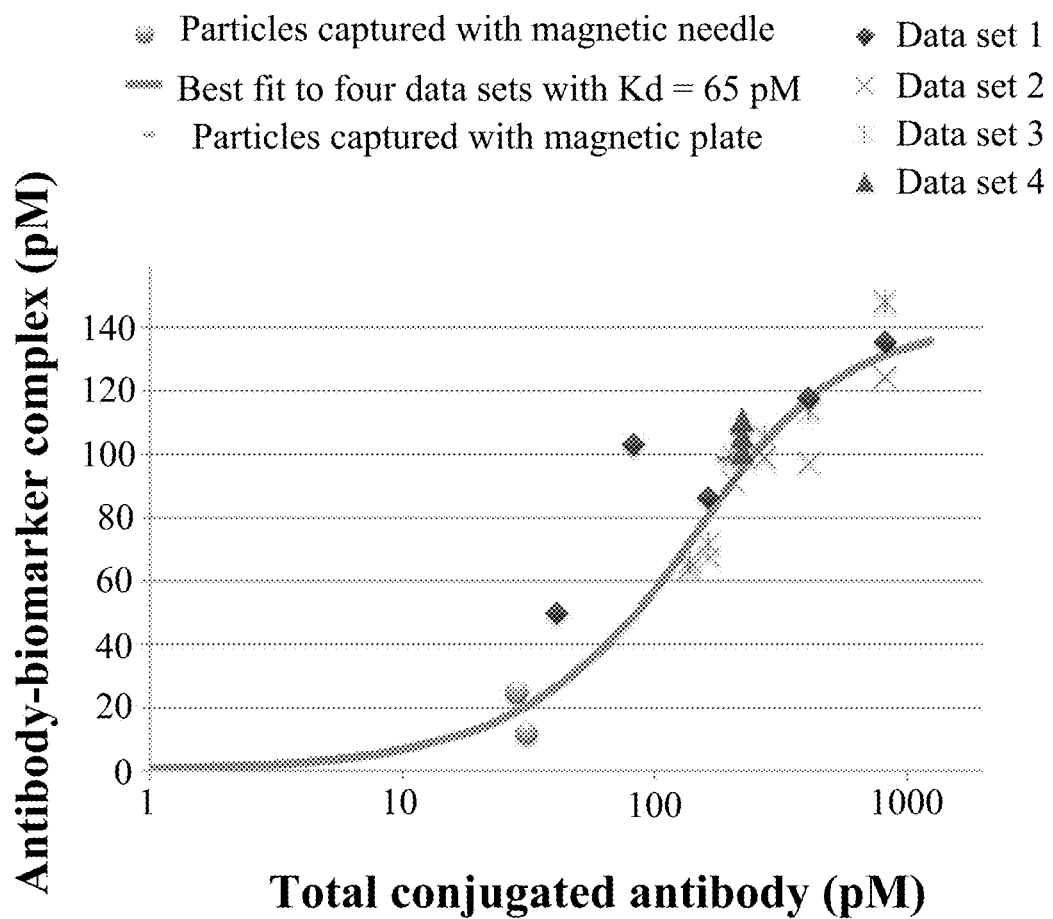
FIG. 12 is a graph showing the calibration curve for Kd determination.

In FIG. 12, the calibration curve represents a simultaneous fit to four independent data sets, each obtained with anti-CTX-II conjugated 1 μm magnetic particles. The best fit was obtained with $K_d$=65 pM. Red points represent the results of quantification of antibody and biomarker obtained in the magnetic needle experiment shown in FIG. 7.

The invention claimed is:

1. A method of assaying a non-cell biomarker in synovial fluid from a subject in need thereof, the method comprising:
administering superparamagnetic particles to a subject in need thereof, wherein the superparamagnetic particles comprise a ligand capable of specifically binding a non-cell biomarker and the subject in need thereof has or is suspected of having osteoarthritis;
inserting a cannulae having a hollow cross-sectional area configured to receive a magnetic needle into a cavity of the subject in need thereof having synovial fluid and the non-cell biomarker in the synovial fluid;
specifically binding the non-cell biomarker in the cavity to the ligand bound to the superparamagnetic particles while the cannulae is inserted in the cavity;
inserting a magnetic needle into the hollow cross-sectional area of the cannulae, wherein the magnetic needle comprises a soft magnetic rod and a magnetic apparatus at a distal end of the soft magnetic rod, wherein a distal end of magnetic apparatus opposite the soft magnetic rod is 30 microns to 80 microns in diameter,
positioning the magnetic apparatus of the magnetic needle in the cavity of the subject;
magnetically coupling one or more superparamagnetic particles specifically bound to the non-cell biomarker to the magnetic apparatus while the magnetic needle is inserted in the cavity of the subject;
removing the magnetic apparatus coupled to one or more superparamagnetic particles specifically bound to the non-cell biomarker from the cavity and the cannulae, wherein no or a negligible amount of synovial fluid is removed from the cavity of the subject;
uncoupling the superparamagnetic particles with specifically-bound non-cell biomarkers from the magnetic apparatus;
releasing the specifically-bound biomarkers from the superparamagnetic particles; and
determining an amount or level of the released non-cell biomarkers from the subject.

2. The method of claim 1, wherein the administering superparamagnetic particles is by injection into the cavity through the hollow cross-sectional area of the cannulae after inserting the cannulae into the cavity and before insertion of the magnetic needle.

3. The method of claim 1, wherein the magnetic apparatus is conical, cylindrical, or pyramidal in shape.

4. The method of claim 1, wherein the magnetic apparatus has a proximal end opposite the distal end between 200 and 500 microns in diameter.

5. The method of claim 1, further comprising the step of determining a disease or condition based on the determined amount or level of the non-cell biomarker.

6. The method of claim 1, wherein the magnetic apparatus comprises neodymium, iron and boron.

7. The method of claim 6, wherein the magnetic apparatus comprises an alloy having the chemical formula of $Nd_2Fe_{14}B$.

8. The method of claim 1, wherein the ligand is an antibody, and wherein the non-cell biomarker comprises a polynucleotide, a polypeptide, or a fragment thereof.

9. The method of claim 8, wherein the polypeptide is an inflammatory mediator, a collagen degradation product, or a fragment thereof.

10. The method of claim 9, wherein the inflammatory mediator is selected from the group consisting of interleukin-1, interleukin-6, tumor necrosis factor, prostaglandin E, and interferon gamma.

11. The method of claim 9, wherein the collagen degradation product is a C-terminal fragment of Type II collagen.

12. A method of treating a joint disease in a subject in need thereof, the method comprising:

administering superparamagnetic particles to a subject in need thereof, wherein the superparamagnetic particles comprise a ligand capable of specifically binding a non-cell biomarker;

inserting a cannulae having a hollow cross-sectional area configured to receive a magnetic needle into a cavity of a joint of the subject in need thereof having synovial fluid and the non-cell biomarker in the synovial fluid;

inserting a magnetic needle into the hollow cross-sectional area of the cannulae, wherein the magnetic needle comprises a soft magnetic rod and a magnetic apparatus at a distal end, wherein a distal end of magnetic apparatus opposite the soft magnetic rod is 30 microns to 80 microns in diameter;

specifically binding the non-cell biomarker to the ligand bound to the superparamagnetic particles while the needle is inserted in the cavity, wherein the non-cell biomarker is a polypeptide and is an inflammatory mediator or a fragment thereof;

magnetically coupling one or more superparamagnetic particles specifically bound to the non-cell biomarker to the magnet while the needle is inserted in the cavity; and removing the magnetic apparatus coupled to one or more superparamagnetic particles specifically bound to the non-cell biomarker from the cavity and the cannulae, wherein no or a negligible amount of synovial fluid is removed from the cavity of the subject.

13. The method of claim 12, wherein the ligand is an antibody.

14. The method of claim 12, wherein the inflammatory mediator is selected from the group consisting of interleukin-1, interleukin-6, tumor necrosis factor, prostaglandin E, and interferon gamma.

15. The method of claim 12, wherein the collagen degradation product is a C-terminal fragment of Type II collagen.

16. The method of claim 12, wherein the magnetic apparatus comprises an alloy having the chemical formula of $Nd_2Fe_{14}B$.

17. The method of claim 12, wherein the administering superparamagnetic particles is by injection into the cavity through the hollow cross-sectional area of the cannulae after inserting the cannulae into the cavity and before insertion of the magnetic needle.

18. The method of claim 12, wherein the subject in need thereof has or is suspected of having osteoarthritis.

19. A method of collecting non-cell biomarkers in synovial fluid from a subject in need thereof, the method comprising:

inserting a magnetic needle into a cavity of the subject,
wherein the magnetic needle comprises a soft magnetic rod and a magnetic apparatus at a distal end of the soft magnetic rod, wherein a distal end of magnetic apparatus opposite the soft magnetic rod is 30 microns to 80 microns in diameter,
wherein the cavity contains synovial fluid and non-cell biomarkers specifically bound to ligands that are bound to superparamagnetic particles;

magnetically coupling the superparamagnetic particles specifically bound to the non-cell biomarkers to the magnetic apparatus while the magnetic needle is inserted in the cavity of the subject;

removing the magnetic needle and magnetic apparatus magnetically coupled to one or more superparamagnetic particles specifically bound to the non-cell biomarkers from the cavity, wherein no or a negligible amount of synovial fluid is removed from the cavity of the subject.

20. The method of claim 19, further comprising inserting a cannulae having a hollow cross-sectional area configured to receive a magnetic needle into the cavity before inserting the magnetic needle, and inserting the magnetic needle into the hollow cross-sectional area of the cannulae and positioning the magnetic apparatus in the cavity after inserting the cannulae.

* * * * *